(12) United States Patent
Hori et al.

(10) Patent No.: US 7,964,213 B2
(45) Date of Patent: Jun. 21, 2011

(54) PATCH AND PRODUCTION METHOD THEREOF

(75) Inventors: Mitsuhiko Hori, Ibaraki (JP); Keiji Yamamoto, Ibaraki (JP); Kensuke Matsuoka, Ibaraki (JP); Yoshihisa Nakano, Ibaraki (JP)

(73) Assignee: Nitto Denko Corporation, Ibaraki-shi (JP)

( * ) Notice: Subject to any disclaimer, the term of this patent is extended or adjusted under 35 U.S.C. 154(b) by 1680 days.

(21) Appl. No.: 10/411,822

(22) Filed: Apr. 11, 2003

(65) Prior Publication Data

US 2003/0203697 A1    Oct. 30, 2003

(30) Foreign Application Priority Data

Apr. 12, 2002    (JP) .................................. 2002-110612

(51) Int. Cl.
*A61F 13/00*    (2006.01)
(52) U.S. Cl. ........................................................ 424/449
(58) Field of Classification Search .................. 424/449, 424/448, 443
See application file for complete search history.

(56) References Cited

U.S. PATENT DOCUMENTS

| | | | |
|---|---|---|---|
| 5,045,553 A * | 9/1991 | Ueda et al. ..................... | 514/344 |
| 5,186,938 A | 2/1993 | Sablotsky et al. | |
| 5,393,529 A * | 2/1995 | Hoffmann et al. ............. | 424/445 |
| 5,462,746 A | 10/1995 | Wolter et al. | |
| 5,601,839 A * | 2/1997 | Quan et al. .................... | 424/448 |
| 5,658,587 A | 8/1997 | Santus et al. | |
| 6,139,867 A | 10/2000 | Muraoka et al. | |
| 6,348,210 B1 | 2/2002 | Gale | |
| 6,436,433 B1 | 8/2002 | Müller | |
| 6,632,906 B1 | 10/2003 | Kamiyama | |
| 6,689,379 B1 | 2/2004 | Bracht | |

FOREIGN PATENT DOCUMENTS

| | | | |
|---|---|---|---|
| EP | 0531938 A1 * | 3/1993 | |
| JP | 64-085911 A | 3/1989 | |
| JP | 02-193915 A | 7/1990 | |
| JP | 07-069870 A | 3/1995 | |
| WO | WO 00/44846 A1 | 8/2000 | |
| WO | WO 00/59483 A2 | 10/2000 | |
| WO | WO 00/64418 A2 | 11/2000 | |

OTHER PUBLICATIONS

Wikipedia 'oxybutynin' (http://en.wikipedia.org/wiki/Oxybutynin), p. 1.*

* cited by examiner

*Primary Examiner* — Robert A Wax
*Assistant Examiner* — Bethany Barham
(74) *Attorney, Agent, or Firm* — Leydig, Voit & Mayer, Ltd.

(57) ABSTRACT

The present invention relates to a patch containing a substrate, a non-crosslinked adhesive layer (A) containing a drug laminated on one surface of the substrate and a crosslinked adhesive layer (B) laminated on the adhesive layer (A). According to the present invention, the percutaneous absorbability of the drug can be improved, and a patch free of problems such as adhesive residue and adhesive bleed can be provided.

13 Claims, No Drawings

PATCH AND PRODUCTION METHOD THEREOF

FIELD OF THE INVENTION

The present invention relates to a patch for percutaneous administration of a drug other than 2-amino-1-(2',5'-dimethoxyphenyl)ethanol and a pharmacologically acceptable salt thereof, and a production method thereof.

BACKGROUND OF THE INVENTION

There have been increasingly developed many percutaneous absorption type pharmaceutical products in recent years for administration of a drug through the skin. Such percutaneous absorption type pharmaceutical products have been receiving high reputation in view of the utility of the administered drug, which is ensured by avoiding primary metabolism in the liver, sustention of pharmacological effect, compliance such as convenience of administration, confirmation of administration and the like. It is therefore advantageous for many other drugs if they can be administered by a method for percutaneous administration through the skin, particularly a drug administration method comprising use of a patch for adhering a drug-containing adhesive layer to the skin.

In the case of many drugs, however, its percutaneous absorbability is extremely low and, for the expected pharmacological effect of the drug to be expressed, the percutaneous absorbability of the drug needs to be improved by a method comprising adding an absorption enhancer represented by an organic liquid component (e.g., long chain fatty acid ester, long chain aliphatic alcohol etc.) to the adhesive layer of a patch, and the like.

The addition of an organic liquid component to an adhesive is extremely useful for improving percutaneous absorbability of the drug to be contained in the adhesive layer. However, when an organic liquid component is added in a large amount, the adhesive is excessively plasticized to reduce its cohesive power, which then causes problems in that the adhesive partially remains on the skin upon peeling off of the patch from the skin after adhesion (i.e., adhesive residue), and a part of the adhesive leaks out from the edge of the adhesive layer during preservation of a patch in a package (i.e., adhesive bleed) and adheres to the inside of the package, thereby preventing the patch from being taken out easily.

To prevent decrease of the cohesive power of an adhesive, the adhesive is generally crosslinked using various crosslinking agents such as isocyanate, metallic chelate compound, epoxy and the like. When an adhesive layer is formed, however, contact of the drug contained in the adhesive with the crosslinking agent results in a reaction of the crosslinking agent with the drug due to the extremely high reactivity of the crosslinking agent, which then causes modification of the crosslinking agent and/or the drug. Therefore, a crosslinking agent cannot be problematically used for prevention of decrease in the cohesive power of the drug-containing adhesive. When an adhesive is crosslinked using a crosslinking agent, drying of the adhesive at a high temperature, UV irradiation or an aging treatment comprising preservation at a high temperature for a certain time are generally preferable for the complete termination of crosslinking of the adhesive and for higher crosslinking degree. When the adhesive contains a drug, however, the stability of the drug contained in the adhesive is problematically disturbed by these treatments.

Accordingly, it is an object of the present invention to provide a patch that avoids problems such as adhesive residue and adhesive bleed, that facilitates addition of a percutaneous absorption agent and improves the percutaneous absorbability of the drug, as well as a production method thereof.

SUMMARY OF THE INVENTION

As a result of the intensive studies by the present inventors in an attempt to solve the above-mentioned problems, it has been found that a patch comprising a substrate, a non-crosslinked adhesive layer containing a drug other than 2-amino-1-(2',5'-dimethoxyphenyl)ethanol and a pharmacologically acceptable salt thereof (to be referred to as an adhesive layer (A) in the present specification), which is laminated on one surface of the substrate, and a crosslinked adhesive layer (to be referred to as a crosslinked adhesive layer (B) in the present specification) laminated on the adhesive layer (A) improves the percutaneous absorbability of the drug and is free of the problems such as adhesive residue and adhesive bleed. In other words, according to the present invention, the use of two kinds of adhesive layers, i.e., the non-crosslinked adhesive layer (A) containing a drug and the crosslinked adhesive layer (B) in said patch obliterates the problem of modification of drug and/or crosslinking agent due to the contact of the drug with the crosslinking agent, and the stability of the drug is not impaired by an aging treatment for crosslinking.

Accordingly, the present invention provides the following.
[1] A patch comprising a substrate, a non-crosslinked adhesive layer (A) containing a drug other than 2-amino-1-(2', 5'-dimethoxyphenyl)ethanol and a pharmacologically acceptable salt thereof, which is laminated on one surface of the substrate, and a crosslinked adhesive layer (B) laminated on the adhesive layer (A).
[2] The patch of the above-mentioned [1], wherein the crosslinked adhesive layer (B) is obtained by crosslinking an adhesive with at least one kind of crosslinking agent selected from the group consisting of an isocyanate crosslinking agent, a metallic chelate crosslinking agent and an epoxy crosslinking agent.
[3] The patch of the above-mentioned [1], wherein the adhesive layer (A) and/or the crosslinked adhesive layer (B) contain(s) an acrylic adhesive.
[4] The patch of the above-mentioned [1], wherein the adhesive layer (A) and/or the crosslinked adhesive layer (B) contain(s) a long chain fatty acid ester and/or a long chain aliphatic alcohol.
[5] The patch of the above-mentioned [4], satisfying at least one of the following (i) and (ii):
(i) the total content of the long chain fatty acid ester and the long chain aliphatic alcohol in the adhesive layer (A) is 25-200 parts by weight per 100 parts by weight of the adhesive in the adhesive layer (A),
(ii) the total content of the long chain fatty acid ester and the long chain aliphatic alcohol in the crosslinked adhesive layer (B) is 25-200 parts by weight per 100 parts by weight of the adhesive in the crosslinked adhesive layer (B).
[6] The patch of the above-mentioned [4], wherein the long chain fatty acid ester is an ester consisting of a fatty acid having 8 to 30 carbon atoms and an alcohol having 1 to 18 carbon atoms and the long chain aliphatic alcohol has 8 to 30 carbon atoms.
[7] The patch of the above-mentioned [1], wherein the content of the drug in the adhesive layer (A) is 0.5-60 wt % of the total weight of the adhesive layer (A).
[8] The patch of the above-mentioned [1], wherein the substrate is a laminate of a plastic film and a non-woven fabric and the adhesive layer (A) is laminated on the non-woven fabric side.

[9] The patch of the above-mentioned [1], wherein the adhesive in the adhesive layer (A) and the adhesive in the crosslinked adhesive layer (B) have the same composition.

[10] A production method of a patch, which comprises the steps of
(1) dissolving a non-crosslinked adhesive and a drug other than 2-amino-1(2',5'-dimethoxyphenyl) ethanol and a pharmacologically acceptable salt thereof in a solvent to give an adhesive solution,
(2) applying the adhesive solution on one surface of a substrate, and drying the adhesive solution to form an adhesive layer (A), or applying the adhesive solution on a separator, drying the adhesive solution to form an adhesive layer and transfer coating the adhesive layer on one surface of a substrate to form an adhesive layer (A), and
(3) forming a crosslinked adhesive layer (B) free of a drug on the adhesive layer (A), in this order.

[11] The method of the above-mentioned [10], wherein the crosslinked adhesive layer (B) is obtained by crosslinking an adhesive with at least one kind of crosslinking agent selected from the group consisting of an isocyanate crosslinking agent, a metallic chelate crosslinking agent and an epoxy crosslinking agent.

DETAILED DESCRIPTION OF THE INVENTION

The present invention is explained in detail in the following.

The drug other than 2-amino-1-(2',5'-dimethoxyphenyl) ethanol and a pharmacologically acceptable salt thereof to be contained in the adhesive layer (A) is not particularly limited as long as it can be absorbed percutaneously. Particularly, when the drug reacts with a crosslinking agent having high reactivity (e.g., isocyanate, metallic chelate compound, epoxy crosslinking agent etc.) to cause modification of the crosslinking agent and the drug per se, the effect of the present invention can be realized. Examples of such drug include a drug having one or more functional groups, which is selected from the group consisting of alcoholic hydroxyl group, amino group, carboxyl group, thiol group, phenolic hydroxyl group, which is specifically exemplified by methoxamine, propranolol, biperiden, tulobuterol, pindolol and the like.

The drug to be contained in the adhesive layer (A) may be a general drug or a topical drug.

Examples of the general drug include corticosteroids, analgesic antiphlogistics, hypnogenic sedatives, tranquilizer, anti-Parkinson's agents, antihypertensives, hypotensive diuretics, vasopressors, antibiotics, general anesthetics, antimicrobials, antifungals, vitamins, coronary vasodilators, antihistamics, antitussives, sex hormones, antidepressants, cerebral circulation improvers, antiemetics, antitumor agents, enzymes and the like. Examples of the topical drug include topical anesthetics, dental antibiotics, disinfectants, prophylaxis and therapeutic agents of infection, antiphlogistics, adrenocortical hormones and the like.

As the adhesive to be used for the adhesive layer (A), a medical adhesive having tackiness at an ambient temperature, such as an acrylic adhesive, a natural rubber adhesive, a synthetic rubber adhesive (e.g., synthetic isoprene rubber, polyisobutyrene rubber, styrene/butadiene rubber, styrene/isoprene/styrene rubber, styrene/butadiene/styrene rubber and the like), a silicone adhesive, a vinyl ester adhesive, a vinyl ether adhesive and the like are preferable. Of these, at least one kind of adhesive selected from the group consisting of acrylic, natural rubber, synthetic rubber and a silicone adhesive is preferably used, which is particularly preferably an acrylic adhesive, from the aspects of the quality and stability of an adhesive and easiness of control of the adhesive properties. The adhesive to be used for the adhesive layer (A) may be used alone or in combination with plural kinds of adhesives where necessary.

The adhesive layer (A) is essentially non-crosslinked. The absence of a crosslinking agent for formation of the adhesive layer (A) contributes to the prevention of degraded stability of the drug due to the contact of the crosslinking agent with the drug and degraded stability of the drug due to an aging treatment for crosslinking.

The above-mentioned acrylic adhesive is not particularly limited and is exemplified by a copolymer of a (meth)acrylate adhesive, preferably an alkyl(meth)acrylate, with a copolymerizable monomer to be mentioned below. For example, a copolymer obtained by copolymerization of 40-99 wt % of alkyl(meth)acrylate and 1-60 wt % of a copolymerizable monomer can be used, with preference given to a copolymer obtained by copolymerization of 50-98 wt % of alkyl(meth)acrylate and 2-50 wt % of a copolymerizable monomer wherein the total weight of the copolymer is 100 wt %. The alkyl(meth)acrylate and the copolymerizable monomer can be respectively used in combination of one or more thereof.

As such alkyl(meth)acrylate, an ester obtained from primary-tertiary alcohol wherein the alkyl group has 2-18, preferably 4-12, carbon atoms and acrylic acid or methacrylic acid can be preferably used.

Examples of thereof include ethyl(meth)acrylate, butyl(meth)acrylate, tert-butyl(meth)acrylate, pentyl(meth)acrylate, hexyl(meth)acrylate, heptyl(meth)acrylate, octyl(meth)acrylate, isooctyl(meth)acrylate, nonyl(meth)acrylate, isononyl(meth)acrylate, decyl(meth)acrylate, undecyl(meth)acrylate, dodecyl(meth)acrylate, 2-ethylhexyl(meth)acrylate and the like.

As the copolymerizable monomer, a monomer having at least one unsaturated double bond in the molecule, which is involved in the copolymerization reaction, and a functional group in the side chain, such as carboxyl group (e.g., (meth)acrylic acid, itaconic acid, maleic acid, maleic anhydride and the like), hydroxyl group (e.g., hydroxyethyl(meth)acrylate, hydroxypropyl(meth)acrylate and the like), sulfoxyl group (e.g., styrene sulfonic acid, allylsulfonic acid, sulfopropyl(meth)acrylate, (meth)acryloyloxynaphthalenesulfonic acid, acrylamide methylpropanesulfonic acid and the like), amino group (e.g., aminoethyl(meth)acrylate, dimethylaminoethyl(meth)acrylate, tert-butylaminoethyl(meth)acrylate and the like), amide group (e.g., (meth)acrylamide, dimethyl(meth)acrylamide, N-butyl(meth)acrylamide, N-methylol(meth)acrylamide, N-methylolpropane(meth)acrylamide and the like), alkoxyl group (e.g., methoxyethyl(meth)acrylate (e.g., 2-methoxyethyl acrylate and the like), ethoxyethyl(meth)acrylate, methoxyethylene glycol(meth)acrylate, methoxydiethylene glycol(meth)acrylate, methoxytriethylene glycol(meth)acrylate, methoxypolyethylene glycol(meth)acrylate, tetrahydrofulfuryl(meth)acrylate and the like) and the like, can be used. As the copolymerizable monomer other than these, for example, (meth)acrylonitrile, methyl(meth)acrylate, and vinyl monomers such as vinyl acetate, vinyl propionate, vinylpyrrolidone (e.g., N-vinyl-2-pyrrolidone and the like), methylvinylpyrrolidone, vinylpyridine, vinylpiperidone, vinylpyrimidine, vinylpiperazine, vinylpyrazine, vinylpyrrole, vinylimidazole, vinyl caprolactam, vinyloxazole, vinylmorpholine and the like can be used.

As the copolymerizable monomer, a carboxyl group-containing monomer and/or a hydroxyl group-containing monomer is/are preferably used from among the above-mentioned monomers, in view of adhesiveness and cohesiveness as the adhesive properties, releasability of the drug contained in the adhesive layer, and the like. They are preferably copolymerized in the range of generally 1-50 wt %, preferably 3-20 wt %. When a vinyl monomer is used, vinyl acetate and N-vinyl-2-pyrrolidone are preferably used in a proportion of generally not more than 40 wt %, preferably not more than 30 wt %.

As the acrylic adhesive, for example, a copolymer of 2-ethylhexyl acrylate and acrylic acid, a copolymer of 2-ethylhexyl acrylate and hydroxyethyl acrylate, a copolymer of 2-ethylhexyl acrylate and methyl methacrylate, a copolymer of 2-ethylhexyl acrylate, 2-methoxyethyl acrylate and vinyl acetate, a copolymer of 2-ethylhexyl acrylate and vinylpyrrolidone, a copolymer of 2-ethylhexyl acrylate, methyl methacrylate and 2-methoxyethyl acrylate, a copolymer of 2-ethylhexyl acrylate, vinylpyrrolidone and acrylic acid, and the like can be used.

The adhesive layer (A) may further contain rosin, rosin derivative, polyterpene resin, coumarone-indene resin, petroleum resin, terpene phenol resin and the like as necessary to increase viscosity.

The content of the drug in the adhesive layer (A) is generally 0.5-60 wt %, preferably 1-50 wt %, particularly preferably 3-40 wt %, of the total weight of the adhesive layer (A).

By setting the content of the drug for generally not less than 0.5 wt %, preferably not less than 1 wt %, particularly preferably not less than 3 wt %, of the total weight of the adhesive layer (A), a sufficient amount of the drug for showing a pharmacological effect can be percutaneously absorbed.

By setting the content of the drug for generally not more than 60 wt %, preferably not more than 50 wt %, particularly preferably not more than 40 wt %, of the total weight of the adhesive layer (A), degradation of the adhesiveness of the adhesive layer (A) can be prevented, and the adhesive layer (A) can be sufficiently adhered to the crosslinked adhesive layer (B).

The adhesive layer (A) can contain an organic liquid component. As the organic liquid component, for example, long chain fatty acid ester, long chain aliphatic alcohol and the like can be used. By adding an organic liquid component such as long chain fatty acid ester, long chain aliphatic alcohol and the like, these components become compatible with the adhesive layer to plasticize the adhesive layer. As a result, the diffusability of the drug in the adhesive layer can be improved, the skin permeability can be promoted and the percutaneous absorbability of the drug can be improved. The organic liquid component such as long chain fatty acid ester, long chain aliphatic alcohol and the like can be used in combination of one or more kinds thereof.

As the long chain fatty acid ester, for example, an ester consisting of a fatty acid having 8 to 30 carbon atoms and an alcohol having 1 to 18 carbon atoms can be used, such as isopropyl myristate, diethyl sebacate, octyl palmitate, ethyl oleate, laurate (e.g., hexyl laurate and the like), fatty acid esters of glycerol (e.g., glycerol monomyristate, glycerol monostearate and the like), fatty acid esters of propylene glycol (e.g., propylene glycol monostearate and the like) and the like.

Examples of the long chain aliphatic alcohol include aliphatic alcohol having 8 to 30 carbon atoms, such as octyl alcohol, decyl alcohol, dodecyl alcohol, oleyl alcohol, isostearyl alcohol, hexyl decanol, octyl dodecanol, lauryl alcohol and the like.

The total content of the organic liquid component in the adhesive layer (A) is generally 25-200 parts by weight, preferably 40-180 parts by weight, particularly preferably 50-150 parts by weight, per 100 parts by weight of the adhesive in the adhesive layer (A).

By setting the content of the organic liquid component in the adhesive layer (A) for generally not less than 25 parts by weight, preferably not less than 40 parts by weight, particularly preferably not less than 50 parts by weight, per 100 parts by weight of the adhesive in the adhesive layer (A), the adhesive layer can be sufficiently plasticized, as a result of which, diffusability of the drug in the adhesive layer can be improved to promote its skin permeability, which in turn results in an improved percutaneous absorbability of the drug.

By setting the content of the organic liquid component in the adhesive layer (A) for generally not more than 200 parts by weight, preferably not more than 180 parts by weight, particularly preferably not more than 150 parts by weight, per 100 parts by weight of the adhesive in the adhesive layer (A), a sufficient cohesive power can be maintained even without crosslinking.

As the adhesive to be used for the crosslinked adhesive layer (B), conventionally used medical adhesives such as acrylic adhesive, a natural rubber adhesive, a synthetic rubber adhesive (e.g., synthetic isoprene rubber, polyisobutyrene rubber, styrene/butadiene rubber, styrene/isoprene/styrene rubber, styrene/butadiene/styrene rubber and the like), a silicone adhesive, a vinyl ester adhesive, a vinyl ether adhesive and the like, which have tackiness at ambient temperature and which are free of rash and the like upon application to the skin surface, are preferable. Of these, at least one kind of adhesive selected from the group consisting of acrylic, natural rubber, synthetic rubber and a silicone adhesive, particularly preferable acrylic adhesive, is preferably used from the aspects of stable quality of adhesive and easy control of adhesive properties. The adhesive to be used for the crosslinked adhesive layer (B) may be used alone or in combination with plural kinds of adhesives where necessary.

The above-mentioned acrylic adhesive is not particularly limited and is exemplified by a copolymer of a (meth)acrylate adhesive, preferably an alkyl(meth)acrylate, with a copolymerizable monomer to be mentioned below. For example, a copolymer obtained by copolymerization of 40-99 wt % of alkyl(meth)acrylate and 1-60 wt % of a copolymerizable monomer can be used, with preference given to a copolymer obtained by copolymerization of 50-98 wt % of alkyl(meth)acrylate and 2-50 wt % of a copolymerizable monomer wherein the total weight of the copolymer is 100 wt %. The alkyl(meth)acrylate and the copolymerizable monomer may be respectively used in combination of one or more thereof.

As such alkyl(meth)acrylate and copolymerizable monomer, those exemplified for the aforementioned adhesive layer (A) can be preferably used.

The copolymerizable monomer in combination of one or more kinds thereof can be copolymerized with alkyl(meth)acrylate, as mentioned above. In view of the adhesive properties such as adhesiveness and cohesiveness and the like, generally 1-50 wt %, preferably 3-20 wt % of at least one of the carboxyl group-containing monomer and the hydroxyl group-containing monomer is copolymerized, and where necessary, the above-mentioned other monomer; for example, vinyl monomer such as vinyl acetate, N-vinyl-2-pyrrolidone and the like is preferably copolymerized in a proportion of generally not more than 40 wt %, preferably not more than 30 wt %.

As the acrylic adhesive, for example, a copolymer of 2-ethylhexyl acrylate and acrylic acid, a copolymer of 2-ethylhexyl acrylate and hydroxyethyl acrylate, a copolymer of 2-ethylhexyl acrylate, vinylpyrrolidone and acrylic acid, and the like can be used.

The crosslinking treatment of the adhesive is not particularly limited and can be conducted by, for example, a conventional method using a crosslinking agent. The crosslinking agent is not particularly limited but the effect of the present invention can be particularly exhibited when a crosslinking agent that reacts with the drug to be contained is caused modification of the crosslinking agent and/or the drug or a crosslinking agent that prefers an aging treatment for completion of crosslinking and improving crosslinking degree is used. Examples of such crosslinking agent include isocyanates (e.g., CORONATE HL: manufactured by NIPPON POLYURETHANE INDUSTRY CO., LTD., and the like), metallic chelate compounds (e.g., ALCH: manufactured by Kawaken Fine Chemicals Co., Ltd., and the like), epoxy (e.g., TEPIC: manufactured by NISSAN CHEMICAL INDUSTRIES LTD., and the like) and the like. The crosslinking agent may be used alone or in combination of plural kinds thereof where necessary.

While the content of the crosslinking agent varies depending on the kind of the crosslinking agent, it is generally 0.01-5 parts by weight, preferably 0.03-3 parts by weight, particularly preferably 0.05-1 part by weight, per 100 parts by weight of the adhesive to be crosslinked.

The adhesive in the adhesive layer (A) and the adhesive in the crosslinked adhesive layer (B) preferably have the same composition for the prevention of interfacial peeling of the adhesive layers upon adhesion of both adhesive layers, promotion of migration of the drug between the both adhesive layers, and improvement of adhesiveness of both adhesive layers. By the "same composition" is meant that the kind of the adhesives is the same. When plural kinds of adhesives are used, the kind and the content of the adhesives are the same.

The crosslinked adhesive layer (B) may further contain rosin, rosin derivative, polyterpene resin, coumarone-indene resin, petroleum resin and terpene phenol resin and the like as necessary to increase the viscosity.

When the crosslinked adhesive layer (B) is prepared by a crosslinking treatment, as mentioned below in the production process of the patch according to the present invention, the absence of a drug in the adhesive avoids inhibition of crosslinking of the adhesive, which can be caused by the contact between the crosslinking agent and the drug. Furthermore, because the crosslinked adhesive layer (B) after completion of the crosslinking treatment is free of an unreacted crosslinking agent of a level that can affect the stability of the drug, the subsequent migration of the drug from the adhesive layer (A) does not pose any problem.

The crosslinked adhesive layer (B) may contain an organic liquid component. As the organic liquid component, for example, long chain fatty acid ester, long chain aliphatic alcohol and the like can be used. By adding an organic liquid component such as long chain fatty acid ester, long chain aliphatic alcohol and the like, the skin permeability of the drug is promoted, and as a result, the percutaneous absorbability of the drug can be improved. In addition, the component is compatible with the adhesive layer and has an effect of plasticizing the adhesive layer. When the patch is adhered to the skin surface, it gives a soft feeling as well. By the abovementioned crosslinking treatment of the adhesive, a suitable cohesive power is afforded to the adhesive, and irritation to the skin upon peeling off after use can be reduced. As the organic liquid component, one or more kinds of long chain fatty acid ester, long chain aliphatic alcohol and the like can be combined for use.

As the long chain fatty acid ester and long chain aliphatic alcohol, those exemplified for the aforementioned adhesive layer (A) can be preferably used.

The total content of the organic liquid component in the crosslinked adhesive layer (B) is generally 25-200 parts by weight, preferably 40-180 parts by weight, particularly preferably 50-150 parts by weight, per 100 parts by weight of the adhesive in the crosslinked adhesive layer (B).

By setting the content of the organic liquid component in the crosslinked adhesive layer (B) for generally not less than 25 parts by weight, preferably not less than 40 parts by weight, particularly preferably not less than 50 parts by weight, per 100 parts by weight of the adhesive in the crosslinked adhesive layer (B), the skin permeability of the drug can be promoted and sufficient plasticizing effect can be exhibited, which in turn reduces irritation to the skin.

By setting the content of the organic liquid component in the crosslinked adhesive layer (B) for generally not more than 200 parts by weight, preferably not more than 180 parts by weight, particularly preferably not more than 150 parts by weight, per 100 parts by weight of the adhesive in the crosslinked adhesive layer (B), reduction of cohesive power due to too much plasticizing of the adhesive layer can be prevented, which in turn obliterates a problem of increased irritation to the skin again due to adhesive residues upon peeling, even if the adhesive was subjected to the crosslinking treatment.

While the substrate of the patch according to the present invention is not particularly limited, a laminate of a plastic film and a non-woven fabric, particularly a laminate film of a plastic film and a non-woven fabric is preferable.

The thickness of the substrate is generally 2-2000 $\mu$m, preferably 2-600 $\mu$m, particularly preferably 10-150 $\mu$m.

As the plastic film to be used for the laminate of a plastic film and a non-woven fabric, for example, films of polyester (e.g.; PET (polyethylene terephthalates) and the like), ethylene/vinyl acetate copolymer, polyethylene, polyurethane, polyolefin, polypropylene and the like can be used. Of these, a polyester film and a polyethylene film are preferable, and a polyester film is particularly preferable because a drug does not easily migrate into the substrate.

The thickness of the plastic film is generally 1-1000 $\mu$m, preferably 2-100 $\mu$m. From flexibility and handling, it is particularly preferably 5-50 $\mu$m.

The non-woven fabric to be used for the laminate of the plastic film and the non-woven fabric is not particularly limited, and can be produced from the materials generally used in the field of the patch. Examples of such material include polyester (e.g., PET (polyethylene terephthalates) and the like), polyethylene, polypropylene, polyamide and the like, with preference given to polyester, polypropylene and polyamide. The basis weight of the non-woven fabric is generally 1-100 $\mu$m, preferably 6-50 $\mu$m$^2$, particularly preferably 6-30 $\mu$m$^2$, in view of fine flexibility and the fine feel of adhesion to the skin upon application.

The thickness of the non-woven fabric is generally 1-1000 $\mu$m, preferably 3-500 $\mu$m, particularly preferably 5-100 $\mu$m.

The patch of the present invention preferably comprises a substrate which is a laminate of a plastic film and a non-woven fabric as mentioned above, wherein the adhesive layer (A) is laminated on the non-woven fabric side. By laminating the adhesive layer (A) on the non-woven fabric layer of the substrate, the anchor force for the substrate can be increased, even when the adhesive to be used for the adhesive layer (A) is a non-crosslinked adhesive and the like having a low cohesive power. Even when the adhesive in the adhesive layer (A) has a low cohesive power, a cohesive failure of the patch upon peeling off from the skin, which is due to insufficient cohesive power, can be prevented.

By laminating the crosslinked adhesive layer (B) on the adhesive layer (A), what is called an adhesive residue, wherein a part of the adhesive remains on the skin surface and the like upon peeling of the patch after application, and the like can be prevented, and what is called an adhesive bleed, wherein a part of the adhesive bleeds out inside the package during preservation, can be prevented, thereby improving performance of taking out the patch from the package.

The thickness of the adhesive layer (A) varies depending on the kind of substrate, the adhesive to be used for the adhesive layer (A), and the like, but it is generally 5-200 μm, preferably 10-150 μm, particularly preferably 20-100 μm.

The thickness of the adhesive layer (A), when an adhesive solution is directly applied to one surface of a substrate (e.g., by comma direct, comma reverse, rip direct, rip reverse, gravure coating and the like) and dried, or what is called a direct coating, is generally the distance between the adhesive layer surface and the boundary of the substrate and the adhesive layer. When an adhesive layer is directly formed on the non-woven fabric surface of the substrate, which is a laminate of a non-woven fabric and a plastic film and the like, the adhesive layer may be embedded in the non-woven fabric, in other words, the adhesive layer is physically embedded in the non-woven fabric or the non-woven fabric is impregnated with the adhesive. In this case, the thickness of the adhesive layer (A) is the distance between the surface of the adhesive layer and the boundary of the non-woven fabric and the plastic film and the like. In the case of what is called a transfer coating, wherein an adhesive solution is applied onto a separator and dried to form an adhesive layer and the adhesive layer is then adhered to one surface of a substrate, the thickness of the adhesive layer (A) refers to the thickness of an adhesive layer formed by applying and drying on a separator.

When the adhesive layer (A) is formed on a non-woven fabric of a substrate consisting of a laminate of a plastic film and a non-woven fabric, the thickness of the adhesive layer (A) is preferably determined in consideration of the thickness of the non-woven fabric of the substrate.

When the adhesive layer (A) is formed by what is called a direct coating, the adhesive layer (A) is preferably not completely embedded in the non-woven fabric, because when the adhesive layer (A) is completely embedded in the non-woven fabric, adhesion to the crosslinked adhesive layer (B) to be laminated further becomes insufficient, which in turn may result in insufficient migration of the drug into the skin surface during application, as well as adhesive residue due to interfacial peeling between the both adhesive layers upon peeling off of the patch after application. The thickness of the adhesive layer (A) outside the non-woven fabric is specifically 0-100 μm, preferably 0-50 μm, more preferably 0-10 μm.

When the adhesive layer (A) outside the non-woven fabric (or adhesive not in contact with the non-woven fabric) is thick, a cohesive failure occurs in the adhesive outside the non-woven fabric, possibly leaving an adhesive residue when, for example, peeling the patch after adhesion and the like. Accordingly, the adhesive layer (A) is preferably almost embedded in the non-woven fabric of the substrate or extremely slightly outside the non-woven fabric.

Of the thickness of adhesive layer (A), the thickness ratio of the adhesive layer within the non-woven fabric layer: adhesive layer outside the non-woven fabric is generally 100:0-25:75, preferably 100:0 to 50:50, from the above-mentioned aspect.

When the adhesive layer (A) is formed by what is called a transfer coating, the adhesive layer (A) is in contact with only the surface of the non-woven fabric, and when the adhesive layer (A) is thick, the adhesive suffers from a cohesive failure, highly possibly leaving an adhesive residue when peeling the patch after adhesion and the like. Thus, before adhesion of the crosslinked adhesive layer (B), the substrate with the adhesive layer (A) is preferably subjected to a press adhesion treatment with a heat roll and the like, thereby sufficiently embedding the adhesive layer (A) in the non-woven fabric layer of the substrate, after which it is adhered to the crosslinked adhesive layer (B).

While the thickness of the crosslinked adhesive layer (B) varies depending on the kind of the adhesive to be used for the adhesive layer (B), and the like, it is generally 5-200 μm, preferably 7-150 μm, particularly preferably 10-100 μm.

The adhesive layer (A) and the crosslinked adhesive layer (B) may contain additives such as antioxidants, various pigments, various fillers, stabilizers, drug-dissolution aids, drug-dissolution suppressors and the like as necessary. In this case, the total amount of the additive is preferably about 2-50 parts by weight per 100 parts by weight of the adhesive.

The patch of the present invention can be produced by, for example, a production method comprising the following steps (1)-(3) in this order. That is, step (1):
dissolving a non-crosslinked adhesive and a drug in a solvent to give an adhesive solution, step (2):
applying (e.g., by comma direct, comma reverse, rip direct, rip reverse, gravure coating and the like) the above-mentioned adhesive solution on one surface of a substrate, and drying the adhesive solution to form an adhesive layer (A), or applying (e.g., by comma direct, comma reverse, rip direct, rip reverse, gravure coating and the like) the above-mentioned adhesive solution on a separator (e.g., polyester film that underwent release treatment and the like), drying the adhesive solution to form an adhesive layer and transfer coating the adhesive layer on one surface of a substrate to form an adhesive layer (A), step (3):
forming a crosslinked adhesive layer (B) free of a drug on the adhesive layer (A).

In step (3), the crosslinked adhesive layer (B) can be obtained by, for example, dissolving the above-mentioned adhesive and the crosslinking agent in a suitable solvent, applying the obtained adhesive solution to a separator (e.g., release treated polyester film and the like) and drying the solution. When preparing the crosslinked adhesive layer (B), it is essential that the mixture of the adhesive and the crosslinking agent should not contain a drug. Because the mixture of the adhesive and the crosslinking agent does not contain a drug, crosslinking of the adhesive is not inhibited by the contact of the crosslinking agent and the drug.

The solvent to be used for the formation of adhesive layer (A) is not particularly limited and one conventionally used as a solvent for an adhesive can be selected in consideration of the kind of the adhesive, reactivity with the drug and the like. For example, ethyl acetate, toluene, hexane, methanol, ethanol or a mixed solution thereof and the like can be used.

The solvent to be used for the formation of the crosslinked adhesive layer (B) is not particularly limited and one conventionally used as a solvent for an adhesive can be selected in consideration of the kind of the adhesive, reactivity with the crosslinking agent and the like. For example, ethyl acetate and the like can be used.

The patch of the present invention comprises the aforementioned substrate, aforementioned adhesive layer (A) laminated on one surface of the substrate and the aforementioned crosslinked adhesive layer (B) laminated on the adhesive layer (A). It is preferable to cover and protect the exposed surface of the crosslinked adhesive layer (B) until just before adhesion to the skin surface, with a release liner such as paper, plastic film and the like release treated by the application of a silicone resin, a fluororesin and the like. When in use, it is released to expose the crosslinked adhesive layer (B) and the patch is adhered to the adhesion site to administer the drug.

The shape of the patch is not limited and includes, for example, tape, sheet and the like.

The dose of the drug in the patch of the present invention varies depending on the kind of the drug, age, body weight and conditions of patients, and the like, and a patch generally containing 0.001-1000 mg of a drug is preferably adhered to 1-200 $cm^2$ of the skin of an adult at a frequency of about 1-7 times per 7 days.

BEST MODE FOR EMBODYING THE INVENTION EXAMPLES

The present invention is explained in more detail by referring to the following Examples and Test Examples. It is needless to say that the present invention can be variously modified within the scope that does not deviate from the technical idea of the present invention. In the following, % means wt %.

Example 1

Crosslinked Adhesive Layer (B)

adhesive 60%
(2-ethylhexyl acrylate/acrylic acid copolymer)
isopropyl myristate 40%
isocyanate crosslinking agent 0.15% (relative to adhesive solid content)
(CORONATE HL: NIPPON POLYURETHANE INDUSTRY CO., LTD.)
drug-containing non-crosslinked adhesive layer (A)
adhesive 46.7%
(2-ethylhexyl acrylate/acrylic acid copolymer)
isopropyl myristate 40%
methoxamine 13.3%

To a solution of an acrylic adhesive (prepared by copolymerization of 2-ethylhexyl acrylate/acrylic acid=95/5) in ethyl acetate were added isopropyl myristate in a proportion of 40% of the plaster weight and CORONATE HL in a proportion of 0.15% of an adhesive solid content, and the solution was applied to a release treated polyester film, so that the thickness after drying became 10 μm, dried and subjected to an aging treatment at 70° C. for 48 hr to give a crosslinked adhesive layer (B).

To a solution of an acrylic adhesive (prepared by copolymerization of 2-ethylhexyl acrylate/acrylic acid=95/5) in a mixed solvent of toluene/methanol were added methoxamine in a proportion of 13.3% and isopropyl myristate in a proportion of 40% of the plaster weight, and this adhesive solution was applied to a non-woven fabric surface of a substrate made of a 6 μm thick PET film and a PET non-woven fabric having a basis weight of 8 $g/m^2$ so that the thickness after drying became 30 μm, dried to give a non-crosslinked adhesive layer (A).

The crosslinked adhesive layer (B) prepared as mentioned above was laminated on the surface of the non-crosslinked adhesive layer (A) to give a methoxamine tape.

Example 2

Crosslinked Adhesive Layer (B)

adhesive 60%
(2-ethylhexyl acrylate/acrylic acid copolymer)
isostearyl alcohol 40%
metallic chelate crosslinking agent 0.3% (relative to adhesive solid content)
(ALCH: Kawaken Fine Chemicals Co., Ltd.)
drug-containing non-crosslinked adhesive layer (A)
adhesive 46.7%
(2-ethylhexyl acrylate/acrylic acid copolymer)
isostearyl alcohol 40%
propranolol 13.3%

To a solution of an acrylic adhesive (prepared by copolymerization of 2-ethylhexyl acrylate/acrylic acid 95/5) in ethyl acetate were added isostearyl alcohol in a proportion of 40% of the plaster weight and ALCH in a proportion of 0.3% of an adhesive solid content, and the solution was applied to a release treated polyester film, so that the thickness after drying became 10 μm, dried and subjected to an aging treatment at 70° C. for 48 hr to give a crosslinked adhesive layer (B).

To a solution of an acrylic adhesive (prepared by copolymerization of 2-ethylhexyl acrylate/acrylic acid=95/5) in a mixed solvent of toluene/methanol were added propranolol in a proportion of 13.3% and isostearyl alcohol in a proportion of 40% of the plaster weight, and this adhesive solution was applied to a release treated polyester film, so that the thickness after drying became 30 μm, dried, and the adhesive layer was applied to a non-woven fabric surface of a substrate, which is made of a 6 μm thick PET film and a polyamide non-woven fabric having a basis weight of 20 $g/m^2$ to give a non-crosslinked adhesive layer (A).

The polyester film of the non-crosslinked adhesive layer (A) was peeled off and the crosslinked adhesive layer (B) prepared as mentioned above was laminated on the plaster surface of the layer (A) to give a propranolol tape.

Example 3

Crosslinked Adhesive Layer (B)

adhesive 70%
(2-ethylhexyl acrylate/acrylic acid/vinylpyrrolidone copolymer)
hexyl decanol 30%
metallic chelate crosslinking agent 0.3% (relative to adhesive solid content)
(ALCH: Kawaken Fine Chemicals Co., Ltd.)
drug-containing non-crosslinked adhesive layer (A)
adhesive 56.7% (2-ethylhexyl acrylate/acrylic acid/vinylpyrrolidone copolymer)
hexyl decanol 30%
biperiden 13.3%

To a solution of an acrylic adhesive (prepared by copolymerization of 2-ethylhexyl acrylate/acrylic acid/vinylpyrrolidone=75/3/22) in ethyl acetate were added hexyl decanol in a proportion of 30% of the plaster weight and ALCH in a proportion of 0.3% of an adhesive solid content, and the solution was applied to a release treated polyester film, so that the thickness after drying became 10 μm, dried and subjected to an aging treatment at 70° C. for 48 hr to give a crosslinked adhesive layer (B).

To a solution of an acrylic adhesive (prepared by copolymerization of 2-ethylhexyl acrylate/acrylic acid/vinylpyrrolidone=75/3/22) in ethanol were added biperiden in a proportion of 13.3% and hexyl decanol in a proportion of 30% of the plaster weight, and this adhesive solution was applied to the surface of a non-woven fabric of a substrate made of a 6 μm thick PET film and a PET non-woven fabric having a basis weight of 8 g/m², so that the thickness after drying became 30 µm, dried to give a non-crosslinked adhesive layer (A).

The crosslinked adhesive layer (B) prepared above was laminated on the plaster surface of the non-crosslinked adhesive layer (A) to give a biperiden tape.

Example 4

Crosslinked Adhesive Layer (B)

adhesive 60%
(2-ethylhexyl acrylate/acrylic acid copolymer)
diethyl sebacate 40%
isocyanate crosslinking agent 0.15% (relative to adhesive solid content)
(CORONATE HL: NIPPON POLYURETHANE INDUSTRY CO., LTD.)
drug-containing non-crosslinked adhesive layer (A)
adhesive 46.7%
(2-ethylhexyl acrylate/acrylic acid copolymer)
lauryl alcohol 40%
propranolol 13.3%

To a solution of an acrylic adhesive (prepared by copolymerization of 2-ethylhexyl acrylate/acrylic acid 95/5) in ethyl acetate were added diethyl sebacate in a proportion of 40% of the plaster weight and CORONATE HL in a proportion of 0.15% of an adhesive solid content, and the solution was applied to a release treated polyester film, so that the thickness after drying became 10 µm, dried and subjected to an aging treatment at 70° C. for 48 hr to give a crosslinked adhesive layer (B).

To a solution of an acrylic adhesive (prepared by copolymerization of 2-ethylhexyl acrylate/acrylic acid=95/5) in a mixed solvent of toluene/methanol were added propranolol in a proportion of 13.3% and lauryl alcohol in a proportion of 40% of the plaster weight, and this adhesive solution was applied to the surface of a non-woven fabric of a substrate made of a 6 µm thick PET film and a PET non-woven fabric having a basis weight of 8 g/m², so that the thickness after drying became 30 µm, dried to give a non-crosslinked adhesive layer (A).

The crosslinked adhesive layer (B) prepared above was laminated on the plaster surface of the non-crosslinked adhesive layer (A) to give a propranolol-tape.

Example 5

In the same manner as in Example 1 except that isopropyl myristate was not added to the non-crosslinked adhesive layer (A) and the crosslinked adhesive layer (B), a methoxamine tape was prepared.

Example 6

In the same manner as in Example 2 except that isostearyl alcohol was not added to the non-crosslinked adhesive layer (A) and the crosslinked adhesive layer (B), a propranolol tape was prepared.

Example 7

In the same manner as in Example 3 except that hexyl decanol was not added to the non-crosslinked adhesive layer (A) and the crosslinked adhesive layer (B), a biperiden tape was prepared.

Example 8

In the same manner as in Example 3 except that the non-crosslinked adhesive layer (A) was applied to a surface of the PET film of the substrate, a biperiden tape was prepared.

Example 9

Crosslinked Adhesive Layer (B)

adhesive 60%
(2-ethylhexyl acrylate/acrylic acid copolymer)
isopropyl myristate 40%
isocyanate crosslinking agent 0.15% (relative to adhesive solid content)
(CORONATE HL: NIPPON POLYURETHANE INDUSTRY CO., LTD.)
drug-containing non-crosslinked adhesive layer (A)
adhesive 46.7%
(polyisobutylene type)
isopropyl myristate 40%
methoxamine 13.3%

To a solution of an acrylic adhesive (prepared by copolymerization of 2-ethylhexyl acrylate/acrylic acid=95/5) in ethyl acetate were added isopropyl myristate in a proportion of 40% of the plaster weight and CORONATE HL in a proportion of 0.15% of an adhesive solid content, and the solution was applied to a release treated polyester film, so that the thickness after drying became 10 µm, dried and subjected to an aging treatment at 70° C. for 48 hr to give a crosslinked adhesive layer (B).

To a solution of a rubber adhesive containing polyisobutylene as a main component in hexane were added methoxamine in a proportion of 13.3% and isopropyl myristate in a proportion of 40% of the plaster weight, and this adhesive solution was applied to the surface of a non-woven fabric of a substrate made of a 6 µm thick PET film and a PET non-woven fabric having a basis weight of 8 g/m² so that the thickness after drying became 30 µm, dried to give a non-crosslinked adhesive layer (A).

The crosslinked adhesive layer (B) prepared above was laminated on the plaster surface of the non-crosslinked adhesive layer (A) to give a methoxamine tape.

Comparative Example 1

In the same manner as in Example 1 except that an isocyanate crosslinking agent was not added to the crosslinked adhesive layer (B), a methoxamine tape was prepared.

Comparative Example 2

Drug-Containing Non-Crosslinked Adhesive Layer adhesive 50%
(2-ethylhexyl acrylate/acrylic acid copolymer)
isopropyl myristate 40%
methoxamine 10%

To a solution of an acrylic adhesive (prepared by copolymerization of 2-ethylhexyl acrylate/acrylic acid=95/5) in a mixed solvent of toluene/methanol were added methoxamine in a proportion of 10% and isopropyl myristate in a proportion of 40% of the plaster weight, and this adhesive solution was applied to a non-woven fabric surface of a substrate made of a 6 µm thick PET film and a PET non-woven fabric having a basis weight of 8 g/m², so that the thickness after drying became 40 µm, dried to give a non-crosslinked adhesive layer.

Comparative Example 3

Drug-Containing Crosslinked Adhesive Layer adhesive 50%
(2-ethylhexyl acrylate/acrylic acid copolymer)
isopropyl myristate 40%
methoxamine 10%
isocyanate crosslinking agent 0.15% (relative to adhesive solid content)
(CORONATE HL: NIPPON POLYURETHANE INDUSTRY CO., LTD.)

To a solution of an acrylic adhesive (prepared by copolymerization of 2-ethylhexyl acrylate/acrylic acid=95/5) in ethyl acetate were added methoxamine in a proportion of 10% and isopropyl myristate in a proportion of 40% of the plaster weight, and CORONATE HL in a proportion of 0.15% of the adhesive solid content, and this adhesive solution was applied to the surface of a non-woven fabric of a substrate made of a 6 µm thick PET film and a PET non-woven fabric having a basis weight of 8 g/m², so that the thickness after drying became 40 µm, dried and subjected to an aging treatment at 70° C. for 48 hr to give a methoxamine-containing crosslinked adhesive layer.

Test Example 1

Permeability Test

The samples of Examples 1-3 and 5-7 obtained above were punched out in 6 mmφ, each was adhered to the center of a shed snake skin (diameter 2 cm), set on a permeability tester (manufactured by VANGARD International Inc., catalog No. VFT02), and the skin permeability of the drug into water on the receptor side was measured. The cumulative amount of permeation per unit area after 24 hr was calculated. The promotion rate of the cumulative amount of permeation of the patches (Examples 1-3) containing an organic liquid component relative to that of the corresponding patches (Examples 5-7) without an organic liquid component is shown in Table 1.

Test Example 2

Adhesion Test

The samples of Examples 1-9 and Comparative Examples 1-3 obtained above were punched out in 10 cm², and each was adhered to the skin of the back of New Zealand white rabbits, which had been sheared and shaved. The samples were peeled off 24 hr later and the adhesive properties relative to during adhesion and after peeling were measured according to the following scores. The results are shown in Table 1.
During adhesion
⊙: Fine adhesiveness in the entirety without lifting or peeling.
○: Lifting and peeling observed to some extent but without practical problem.
x: Peeling or falling in the area of 50% or above.
After peeling
⊙: Fine peeling without adhesive residue on the adhered area.
○: Adhesive residue observed to some extent but without practical problem.
x: Adhesive residue observed in the entirety.

Test Example 3

Taking Out Test

The samples of Examples 1-9 and Comparative Examples 1-3 obtained above were punched out in 10 cm², each was sealed in a polyacrylonitrile package, and preserved at 50° C. The package was opened one month later and take out performance from the package was evaluated according to the following scores. The results are shown in Table 1.
⊙: No adhesive bleed was observed and the sample could be smoothly taken out.
○: Partial adhesive bleed was observed but the sample could be taken out.
x: Intensive adhesive bleed was observed and the sample could not be taken out.

TABLE 1

| Samples | Permeability test (promotion rate) | Adhesion test During adhesion | Adhesion test After peeling | Taking out test |
|---|---|---|---|---|
| Example 1 | 15.6 | ⊙ | ⊙ | ⊙ |
| Example 2 | 13.2 | ⊙ | ⊙ | ⊙ |
| Example 3 | 9.5 | ⊙ | ⊙ | ⊙ |
| Example 4 | — | ⊙ | ⊙ | ⊙ |
| Example 5 | 1 | ⊙ | ⊙ | ⊙ |
| Example 6 | 1 | ⊙ | ⊙ | ⊙ |
| Example 7 | 1 | ⊙ | ⊙ | ⊙ |
| Example 8 | — | ○ | ○ (partial anchor failure) | ○ |
| Example 9 | — | ○ | ○ (partial interfacial peeling) | ○ |
| Comparative Example 1 | — | ⊙ | x (cohesive failure) | x |
| Comparative Example 2 | — | ⊙ | x (cohesive failure) | x |
| Comparative Example 3 | — | ⊙ | x (cohesive failure) | x |

—: not measured

According to the present invention, the percutaneous absorbability of a drug can be improved and a patch free of the problems such as adhesive residue and adhesive bleed can be provided.

This application is based on a patent application No. 2002-110612 filed in Japan, the contents of which are all hereby incorporated by reference.

What is claimed is:

1. A patch comprising a substrate, a non-crosslinked adhesive layer (A) containing a drug other than 2-amino-1-(2',5'-dimethoxyphenyl)ethanol and a pharmacologically acceptable salt thereof, which is laminated on one surface of the substrate, and a crosslinked adhesive layer (B) laminated on the adhesive layer (A),
wherein the adhesive layer (A) comprises 25-200 parts by weight of an organic liquid component per 100 parts by weight of the adhesive in the adhesive layer (A),
wherein the adhesive layer (A) comprises a long chain fatty acid ester and/or a long chain aliphatic alcohol,
wherein the adhesive layer (B) comprises 25-200 parts by weight of an organic liquid component per 100 parts by weight of the adhesive in the adhesive layer (B), and wherein the drug has one or more functional groups selected from the group consisting of an alcoholic hydroxyl group, an amino group, a carboxyl group, a thiol group, and a phenolic hydroxyl group.

2. The patch of claim 1, wherein the crosslinked adhesive layer (B) is obtained by crosslinking an adhesive with at least one kind of crosslinking agent selected from the group consisting of an isocyanate crosslinking agent, a metallic chelate crosslinking agent and an epoxy crosslinking agent.

3. The patch of claim 1, wherein the adhesive layer (A) and/or the crosslinked adhesive layer (B) comprise(s) an acrylic adhesive.

4. The patch of claim 1, wherein the crosslinked adhesive layer (B) comprises a long chain fatty acid ester and/or a long chain aliphatic alcohol.

5. The patch of claim 4, satisfying at least one of the following (i) and (ii):
(i) the total content of the long chain fatty acid ester and the long chain aliphatic alcohol in the adhesive layer (A) is 25-200 parts by weight per 100 parts by weight of the adhesive in the adhesive layer (A),
(ii) the total content of the long chain fatty acid ester and the long chain aliphatic alcohol in the crosslinked adhesive layer (B) is 25-200 parts by weight per 100 parts by weight of the adhesive in the crosslinked adhesive layer (B).

6. The patch of claim 4, wherein the long chain fatty acid ester is an ester consisting of a fatty acid having 8 to 30 carbon atoms and an alcohol having 1 to 18 carbon atoms and the long chain aliphatic alcohol has 8 to 30 carbon atoms.

7. The patch of claim 1, wherein the content of the drug in the adhesive layer (A) is 0.5-60 wt % of the total weight of the adhesive layer (A).

8. The patch of claim 1, wherein the substrate is a laminate of a plastic film and a non-woven fabric and the adhesive layer (A) is laminated on the non-woven fabric side.

9. The patch of claim 1, wherein the adhesive in the adhesive layer (A) and the adhesive in the crosslinked adhesive layer (B) have the same composition.

10. A production method of a patch, which comprises the steps of
(1) dissolving a non-crosslinked adhesive and a drug other than 2-amino-1-(2',5'-dimethoxyphenyl)ethanol and a pharmacologically acceptable salt thereof in a solvent to give an adhesive solution,
(2) applying the adhesive solution on one surface of a substrate, and drying the adhesive solution to form an adhesive layer (A), or applying the adhesive solution on a separator, drying the adhesive solution to form an adhesive layer and transfer coating the adhesive layer on one surface of a substrate to foam an adhesive layer (A), and
(3) forming a crosslinked adhesive layer (B) free of a drug on the adhesive layer (A), in this order,
wherein the drug has one or more functional groups selected from the group consisting of an alcoholic hydroxyl group, an amino group, a carboxyl group, a thiol group, and a phenolic hydroxyl group.

11. The method of claim 10, wherein the crosslinked adhesive layer (B) is obtained by crosslinking an adhesive with at least one kind of crosslinking agent selected from the group consisting of an isocyanate crosslinking agent, a metallic chelate crosslinking agent and an epoxy crosslinking agent.

12. The patch of claim 1, wherein the total content of the long chain fatty acid ester and the long chain aliphatic alcohol in the adhesive layer (A) is 25-200 parts by weight per 100 parts by weight of the adhesive in the adhesive layer (A).

13. The patch of claim 1, wherein the long chain fatty acid ester is an ester consisting of a fatty acid having 8 to 30 carbon atoms and an alcohol having 1 to 18 carbon atoms and the long chain aliphatic alcohol has 8 to 30 carbon atoms.

* * * * *